United States Patent
Carstens

(10) Patent No.: US 7,169,188 B2
(45) Date of Patent: Jan. 30, 2007

(54) SEALING SLEEVE FOR SEALING RESIDUAL LIMB IN A PROSTHETIC SOCKET

(75) Inventor: Felix Carstens, Neustadt an der Weinstrasse (DE)

(73) Assignee: Ossur hf, Reykjavik (IS)

( * ) Notice: Subject to any disclaimer, the term of this patent is extended or adjusted under 35 U.S.C. 154(b) by 132 days.

(21) Appl. No.: 10/487,928

(22) PCT Filed: Aug. 23, 2002

(86) PCT No.: PCT/DE02/03085

§ 371 (c)(1),
(2), (4) Date: Feb. 27, 2004

(87) PCT Pub. No.: WO03/024370

PCT Pub. Date: Mar. 27, 2003

(65) Prior Publication Data

US 2004/0236434 A1    Nov. 25, 2004

(30) Foreign Application Priority Data

Aug. 30, 2001    (DE) ................................. 101 42 492

(51) Int. Cl.
*A61F 2/80*    (2006.01)
*A61F 2/78*    (2006.01)
*A61F 2/60*    (2006.01)

(52) U.S. Cl. .............................. 623/34; 623/35; 623/37

(58) Field of Classification Search ................... 623/32, 623/33, 34, 35, 36, 37; D24/155; 602/26, 602/62, 63
See application file for complete search history.

(56) References Cited

U.S. PATENT DOCUMENTS

| | | | | |
|---|---|---|---|---|
| 980,457 A | * | 1/1911 | Toles ........................... | 623/37 |
| 1,398,824 A | | 11/1921 | Abrams | |
| 1,893,853 A | * | 1/1933 | Tullis .......................... | 623/37 |
| 2,530,285 A | | 11/1950 | Catranis ........................ | 3/3 |
| 2,533,404 A | | 12/1950 | Sharp et al. ................... | 3/9 |
| 2,634,424 A | * | 4/1953 | O'Gorman ..................... | 623/37 |
| 2,671,225 A | | 3/1954 | Schoene et al. ................ | 3/19 |
| 2,808,593 A | | 10/1957 | Andersen ....................... | 3/17 |
| 3,393,407 A | | 7/1968 | Kandel .......................... | 3/20 |
| 3,671,980 A | * | 6/1972 | Baird ............................ | 623/37 |
| 4,923,474 A | | 5/1990 | Klasson et al. ................ | 623/33 |
| 5,007,937 A | | 4/1991 | Fishman et al. ............... | 623/34 |
| 5,139,523 A | | 8/1992 | Paton et al. ................... | 623/37 |

(Continued)

FOREIGN PATENT DOCUMENTS

DE    745 981    12/1943

(Continued)

*Primary Examiner*—Corrine McDermott
*Assistant Examiner*—Thomas J. Sweet
(74) *Attorney, Agent, or Firm*—Bacon & Thomas, PLLC

(57) ABSTRACT

A prosthetic socket is fitted at a distance from its distal end with an annular chamber. This annular chamber is closed by a contour-conforming sealing wall facing the inner side of the prosthetic socket, said wall being designed to hermetically rest against the outer side of a residual limb. The space between the contour-conforming wall and the hard prosthetic socket is vented to atmosphere, whereby self-enhancing compression by the sealing wall against a residual limb arises when a partial vacuum arises in the distal prosthetic socket between the wall and the distal end. A liner having a sealing wall also is disclosed.

20 Claims, 4 Drawing Sheets

U.S. PATENT DOCUMENTS

| | | | |
|---|---|---|---|
| 5,163,965 A | 11/1992 | Rasmusson et al. | 623/36 |
| 5,226,918 A | 7/1993 | Silagy et al. | 623/32 |
| 5,314,496 A | 5/1994 | Harris et al. | 623/31 |
| 5,376,129 A | 12/1994 | Faulkner et al. | 623/33 |
| 5,376,131 A | 12/1994 | Lenze et al. | 623/34 |
| 5,549,709 A * | 8/1996 | Caspers | 623/24 |
| 5,658,353 A | 8/1997 | Layton | 623/34 |
| 5,702,489 A | 12/1997 | Slemker | 623/34 |
| 5,718,925 A * | 2/1998 | Kristinsson et al. | 425/2 |
| 5,728,170 A | 3/1998 | Becker et al. | 623/37 |
| 5,735,906 A | 4/1998 | Caspers | 623/34 |
| 5,888,216 A | 3/1999 | Haberman | 623/36 |
| 5,904,722 A | 5/1999 | Caspers | 623/34 |
| 5,931,872 A | 8/1999 | Lohmann | 623/36 |
| 5,972,036 A | 10/1999 | Kristinsson et al. | 623/33 |
| 6,149,691 A * | 11/2000 | Fay et al. | 623/37 |
| 6,231,616 B1 | 5/2001 | Helmy | 623/34 |
| 6,231,617 B1 | 5/2001 | Fay | 623/36 |
| 6,273,918 B1 | 8/2001 | Yuhasz et al. | 623/33 |
| 6,287,345 B1 | 9/2001 | Slemker et al. | 623/34 |
| 6,361,568 B1 | 3/2002 | Hoerner | 623/32 |
| 6,508,842 B1 | 1/2003 | Caspers | 623/32 |
| 6,554,868 B1 | 4/2003 | Caspers | 623/34 |
| 6,585,774 B2 | 7/2003 | Dean, Jr. et al. | 623/37 |
| 6,645,253 B2 | 11/2003 | Caspers | 623/26 |
| 6,726,726 B2 | 4/2004 | Caspers | 623/34 |
| 6,761,742 B2 | 7/2004 | Caspers | 623/34 |
| 2001/0005798 A1 | 6/2001 | Caspers | 623/34 |
| 2001/0016781 A1 | 8/2001 | Caspers | 623/34 |
| 2002/0040248 A1* | 4/2002 | Karason | 623/37 |
| 2002/0087215 A1 | 7/2002 | Caspers | 623/34 |
| 2002/0091449 A1 | 7/2002 | Caspers et al. | 623/34 |
| 2002/0099450 A1* | 7/2002 | Dean et al. | 623/26 |
| 2003/0191539 A1 | 10/2003 | Caspers | 623/35 |
| 2004/0030411 A1 | 2/2004 | Caspers | 623/37 |
| 2004/0098136 A1 | 5/2004 | Caspers | 623/34 |
| 2004/0122528 A1 | 6/2004 | Egilsson | 623/34 |
| 2004/0143345 A1 | 7/2004 | Caspers | 623/36 |
| 2004/0167638 A1 | 8/2004 | Caspers | 623/27 |
| 2004/0181290 A1 | 9/2004 | Caspers | 623/34 |
| 2004/0236434 A1 | 11/2004 | Carstens | 623/34 |
| 2004/0243251 A1 | 12/2004 | Carstens | 623/34 |
| 2004/0243252 A1 | 12/2004 | Carstens | 623/34 |

FOREIGN PATENT DOCUMENTS

| | | |
|---|---|---|
| DE | 813190 | 7/1951 |
| DE | 1 795 809 | 9/1959 |
| DE | 2 060 239 | 12/1970 |
| DE | 2 540 138 | 3/1977 |
| DE | 3 221 920 | 4/1983 |
| DE | 3 508 919 | 9/1986 |
| DE | 9 419 208.1 | 11/1994 |
| GB | 267988 | 3/1927 |
| GB | 2 069 847 | 9/1981 |
| GB | 2 087 727 | 6/1982 |
| JP | 07155343 A | 6/1995 |
| WO | 00/74611 A2 | 12/2000 |
| WO | 01/54631 A1 | 8/2001 |
| WO | 03/099173 A1 | 12/2003 |

* cited by examiner

SEALING SLEEVE FOR SEALING RESIDUAL LIMB IN A PROSTHETIC SOCKET

This application is a national stage filing of PCT/DE02/03085 having a filing date of 23 Aug. 2002, which has the benefit of priority of DE 101 42 492.2 filed 30 Aug. 2001.

BACKGROUND

A. Field of the Invention

This invention relates to sealing sleeves for sealing residual limbs in suction retention prosthetic sockets.

B. Related Art

Residual limb are inserted like pistons in cup-shaped prosthetic sockets. It is therefore known to utilize ambient air pressure and partial vacuum to retain a prosthetic socket on a residual limb. The residual limb for this effect must be kept hermetically sealed against the inner prosthetic socket wall or against a liner donned over the residual limb.

When sealing is adequate, a force applied to remove the prosthetic socket from the residual limb will generate a partial vacuum acting against it. On the other hand, the force of retention collapses immediately when air enters any gap between the residual limb and the prosthetic socket.

European patent document EP 0 632 765 discloses a prosthetic socket fitted with a seal which maintains sealing between a residual limb and a prosthetic socket.

For such purpose, the prosthetic socket is fitted with a peripheral groove located at a distance from its distal end and which receives a sealing ring. The sealing ring consists of an annular core coated with a layer of elastomer. A sealing lip is formed on the ring and extends toward the inside volume of the prosthetic socket.

The purpose of the sealing lip—which hugs the skin of the residual limb—is to compensate for the fluctuations in diameter of the residual limb. Because the prosthetic socket is made of a rigid material, its inside width is constant. On the other hand, the residual limb volume changes over the long and short-terms. The long-term fluctuations are caused by changes in tissue volume, whereas the short-term fluctuations, for example, depend on the blood pressure and circulation in the residual limb. It is known that at higher temperatures the extremities tend to swell while at lower temperatures their diameters decrease. This phenomenon may be observed, for instance, even in a healthy individual under his/her watch wristband.

The lip seal is folded toward the closed prosthetic socket end when the patient inserts the residual limb into the prosthetic socket. The lip seal will then rest against the residual limb solely on account of being prestressed.

The moment a force is applied to remove the prosthetic socket from the residual limb, a slight partial vacuum is set up between the residual limb and the prosthetic socket volume within the distal end and the lip seal. The magnitude of the said partial pressure is approximately proportional to the enlargement of the annular gap between the residual limb and the prosthetic socket.

In the known design, the pressure gradient at the lip seal is in a direction that causes lifting of the lip seal from the residual limb, thereby permitting air to enter the annular gap and, because of the ensuing loss of suction, retention is lost.

The magnitude of the partial vacuum needed to detach the sealing lip depends on the radial prestressing force pressing the sealing lip against the residual limb. It has been observed that a comparatively large prestressing force is required, which in turn may entail interference with blood circulation in the region between the sealing lip and the distal end of the residual limb.

BRIEF SUMMARY OF THE INVENTION

Based on the above state of the art, it is the objective of the present invention to create a prosthetic socket or a sealing sleeve which will assure good air tight sealing between a residual limb and a prosthetic socket without requiring more than slight prestressing forces.

The prosthetic socket according to the present invention is fitted near its proximal opening, that is away from a distally closed end, with an annular chamber extending preferably along the full inside periphery of the cup-shaped inside volume of the prosthetic socket. Said chamber runs in a manner of speaking like a ring about the inside surface of the prosthetic socket and conforms to its contour.

In conventional manner, the contour and the volume of the inner volume of the prosthetic socket are matched to the kind of socket and the kind of prosthesis used.

The chamber is closed by a wall facing toward the inner volume of the prosthesis socket and the wall is made of a flexible, contour-conforming material. The wall is intended to lie in an air tight manner against the skin of a residual limb or, in the event a liner is used, against the outer surface of the liner. A pressure balancing duct assures that at least atmospheric pressure always will be present in the chamber.

When, according to the device of the invention, a force pulls the prosthetic socket away from a residual limb located in the socket, a partial vacuum arises in the gap between the residual limb and the prosthetic socket in the region between the chamber and the socket distal end. Because the chamber interior is vented at atmospheric pressure, the pressure gradient at the wall tends to compress the flexible, contour conforming wall more hermetically and harder against the residual limb skin or the liner on the limb.

Accordingly, and contrary to the prior art, said partial vacuum in the product of the present invention increases compression and hence improves air tight sealing.

According to the solution of the present invention, the air tight sealing effect in the presence of a partial vacuum no longer depends on a prestressing force applied by the seal. Instead, according to the device of the present invention, the sealing force is actuated automatically as a function of the partial vacuum and will become greater as the partial vacuum increases.

The flexible, contour conforming wall may be maintained against the residual limb with very low levels of initial force.

In order to generate the required basic prestressing force, several techniques may be used.

One technique consists in manufacturing the flexible, contour-conforming wall from an elastic material, namely as a cuff-shaped structure that has a diameter less than the inside diameter of the prosthetic socket at the desired location of the chamber. If now the rims of this cuff member are connected to the inside of the prosthetic socket, the elastic material will be stretched while the intermediate area remains substantially unstretched. In this manner, a required inward prestressing force will be obtained.

Another technique is to insert a ring into the chamber so that this ring will correspondingly curve the contour-conforming cuff-like wall inwardly.

Lastly the main area of the chamber inner volume may be configured in the very wall of the prosthetic socket, namely in the form of a peripheral groove in the inner wall of the prosthetic socket. This groove is spanned on the side facing the inner volume of the socket by a flexible and hermetic sealing wall extending continuous with the smooth contour of the socket inner wall.

In the simplest mode, the pressure balancing duct may be an ordinary borehole passing through the socket wall connecting the chamber inner volume with the external atmosphere.

The same basic design principle also may be applied to a sealing sleeve that may be donned over a residual limb before insertion of the limb in a prosthetic socket. In this case a cuff-like flexible sleeve would be fitted with a peripheral chamber located at the outside of and at a distance away from the distal end of the sleeve. Again the chamber will be fitted with a contour-conforming wall sealing which now however is present on the outer side of the sleeve and extends radially outwardly. When the prosthetic socket is being worn, the chamber and sealing wall seals off the inner wall of the prosthetic socket against the residual limb. Again, the chamber is vented to external atmosphere through a pressure balancing duct. The pressure balancing duct runs in the sleeve wall toward the proximal rim of the sleeve and is provided with a shape such that even when the sleeve and the prosthetic socket are worn, it will not be closed up.

It is understood that the above-mentioned new sealing techniques also may be applied to those sockets which are additionally fitted with mechanical locking devices. Illustratively, the prosthetic socket fitted with the chamber may be used jointly with a liner having a mechanical locking device at the distal end thereof and connected in an interlocking manner to the prosthetic socket, provided that the mechanical lock is sufficiently air tight. Also, the socket of the invention including the chamber may be used for a below-knee prosthesis or arm prosthesis in which parts of the prosthetic socket project beyond respective condyle, which are held in a tongs-like manner.

Lastly the said chamber need not necessarily extend at a constant height within the prosthetic socket or on the sleeve outer side. Said chamber in fact may run in an undulating manner and accordingly it may be mounted at those locations offering optimal air tight sealing.

Where particular anatomical conditions ensure that given residual limb zones will hermetically press against the socket inner wall, the said sealing chamber then need not necessarily run over the full inner socket periphery or the full outer liner periphery.

Further developments of the invention are claimed in the dependent claims. Even combinations which are not the objects of an explicit illustrative embodiment should be construed as being claimed.

DESCRIPTION OF THE DRAWINGS

The appended drawing illustrates embodiments of the present invention.

DETAILED DESCRIPTION

Figure 1:
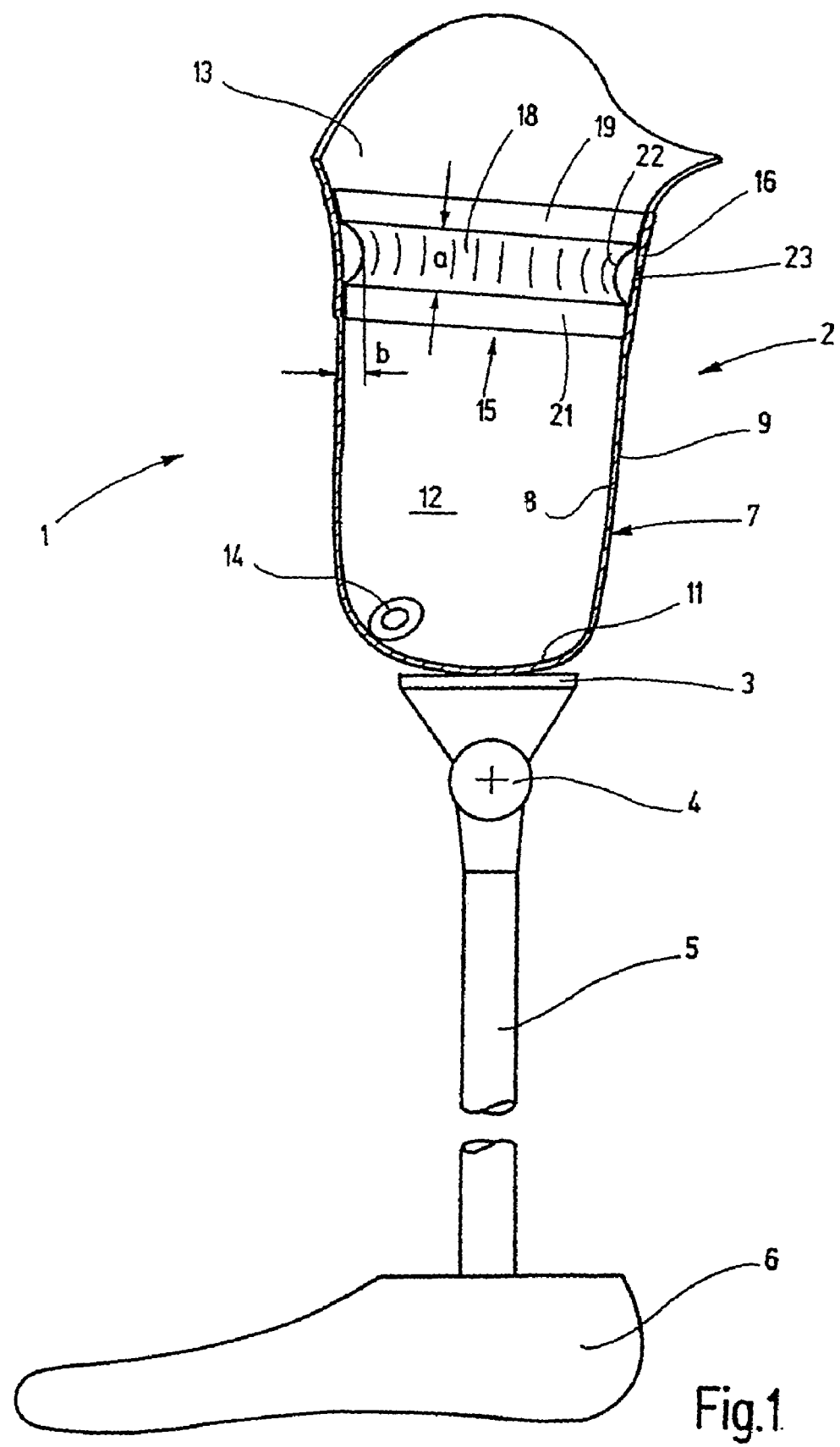
FIG. 1 is a longitudinal section of an above-the-knee prosthesis including a prosthetic socket according to the invention.

In a highly diagrammatic manner, FIG. 1 shows an exemplary above-the-knee prosthesis 1 of the invention. The prosthesis 1 comprises a prosthetic socket 2 connected by an adapter 3 to an artificial knee joint 4. An artificial lower-leg having a foot 6 is connected to the artificial knee joint 4.

The prosthetic socket 2 is composed of a socket wall 7 having an inner wall 8 and an outer wall 9 and a socket distal end 11. The socket distal end 11 merges integrally into the socket wall 7 at the lower end of the wall. Jointly with the inner socket wall 8, the socket distal end 11 subtends a substantially cup-shaped inner volume 12 which is accessible through a proximal residual limb insertion opening at the proximal end. The length of the inside volume 12 and its shape depend on the kind of residual limb and the kind of prosthetic treatment involved. The specific nature of the inside volume 12 is not otherwise significant.

The prosthetic socket 2 is a so-called suction-socket affixed to the residual limb by a partial vacuum.

In order that the air may escape ahead of the residual limb when the latter enters the prosthetic socket 2, a selectively actuated valve 14 is mounted in the transition region between the socket wall 7 and the end 11.

Suction sockets are essentially held in place against the residual limb by partial vacuum. To maintain this partial vacuum, a chamber 15 is provided near the proximal insertion opening 13 and therefore away from the socket end 11. This chamber 15 extends peripherally as a closed ring along the socket wall 7 along its inside surface 8. Accordingly the chamber 15 annularly extends around the inside space 12.

One of the chamber walls is a correspondingly annular zone 16 of the socket wall 7, and an elastic and annular sealing wall 18 spans the inwardly facing wall 8. The sealing wall 18 is situated peripherally on the inside surface 8 of the socket wall 7.

The material of the sealing wall 18 is selected to be flexible, elastically stretchable and able to conform to the local contours of a residual limb located in the socket.

At its rim, the siding wall 18 is adhesively bonded along an appropriate area along two narrow strips 19 and 21 on the inside 8 wall of socket 7. The two narrow strips 19 and 21 are spaced a distance from each other. A band-like segment 22 extends between the narrow strips 19 and 21 and, on account of the pre-tension of the band 18, it curves inward.

Such a configuration is attained if the sealing wall 18 is formed into a cuff the inside diameter of which, in its relaxed state, is smaller than the cross-sectional circumference of the socket 2 at the level of chamber 15. The strip shaped middle region 22 is held extending inwardly when the rim strips 19 and 21 are stretched and bonded in place in the socket.

In this manner the inside volume of the chamber 15 assumes the shape of a ring which is peripherally closed around the socket inside volume 12.

At the level of the chamber 15 and between the two rim strips 19 and 21 the socket wall 7 includes a borehole 23 acting as a pressure balancing duct. The inside volume of the chamber 15 communicates through the borehole 23 with the external atmosphere.

The height b of the middle zone 22 relative to the inside surface 8 is between 0.5 and 3 cm, that is the cross-section of the inside volume 12 in this zone decreases by 1 cm to 6 cm in the central zone 22

The width a of the inwardly concave sealing wall segment 22 is between 2 cm and 10 cm.

Operation of the new prosthetic socket 2 is discussed below in relation to FIG. 2.

When putting on the prosthesis, the patient inserts a residual limb 25 through the insertion opening 13 into the inside volume 12 of the prosthetic socket 2. During this process, air may escape through the valve 14. Insertion ends as soon as the residual limb 25 no longer can penetrate the prosthetic socket 2 any deeper.

After the prosthetic socket 2 has received the residual limb and depending on the conicity of the prosthetic socket 25, the inwardly curving sealing wall in the form of the inwardly curving sealing wall 18 will make contact eventually with the outside of the residual limb 25 and the inside volume of the chamber 15 will be reduced. The material of the sealing wall segment 22, being elastically stretchable, will conform to the outside of the residual limb 25 smoothly and be wrinkle-free as shown.

When above the "outside" of the residual limb 25 is mentioned, illustratively this may refer to the bare skin treated with a skin care product, or just as well the outer side of a previously donned liner.

The gap space, which on one hand is bounded by the residual limb 25 on one side and by the inside surface 8 in the other side, is sealed off toward the insertion opening 13 by the residual limb 25 and the sealing wall segment 22 resting as an air tight seal against the residual limb.

When in use, for instance during lifting the leg prosthesis from the ground such as while walking, the acquired momentum of the prosthesis generates a force between the residual limb 25 and the prosthetic socket 2 which tends to pull said socket 2 from the residual limb 25, thereby generating a partial vacuum in the area of the gap space. This partial vacuum acts on the side of the curved and sealing zone 22 of the sealing wall adjacent the residual limb, whereas atmospheric pressure exists on the opposite side in the region of the inside volume of the chamber 15. The narrow band segment 22 therefore is forced directly proportionally to the magnitude of the partial vacuum against the outside of the residual limb 25. Thus the sealing effect is reliably maintained.

Even if, because of wall elasticity, there would be a less than filled gap space or a very high pulling force, an air tight seal still will be maintained. The compression increases with partial vacuum regardless of the initial prestressing force with which the elastic wall segment 22 is pressed against the outside of the residual limb 25.

The compression which the wall segment 22 applies in its relaxed state need only be enough to provide an initial air tight seal.

The low prestressing/tensioning force increases the wear comfort of the prosthetic socket of the invention because practically no radial force is applied on the residual limb 25 in the region of the chamber 15 while ensuring an air tight seal. The inside width left free by the projecting wall segment 22 need only be large enough such that in the presence of all naturally occurring volume fluctuations of the residual limb, an air tight seal will be maintained against the residual limb in the region of the chamber 15.

In order to withdraw the prosthetic socket 2, the user opens the valve 14 to allow air to enter from below the inside volume 12.

The shown embodiment is applicable both for residual limbs containing comparatively substantial tissue—for instance above-knee prostheses—and for residual limbs including relatively high bone content underneath the skin, for instance below-knee residual limbs.

Depending on the particular residual limb and specific conditions, the chamber 15 may be designed as described above, as a closed ring, or only in those zones along the inner wall 8 where leakages may be expected.

Preferably, the chamber 15, that is the seal, may be moved as close as possible to the proximal end. While the relative change in volume at that location, and hence the relative change in pressure, is less than for a distal position of the chamber 15, the redundancy so attained is more advantageous in the event of minor leakages because a substantial quantity of air must enter before a significant pressure rise can materialize as compared to the case of a distal location.

In the embodiment of FIG. 1, the chamber 15 is bounded toward the inside volume 12 virtually by a cuff the rims of which are prestressed and pulled outward.

There is also the possibility of making the chamber by folding parts of the sealing wall 18 over the rim of the insertion opening 13.

Figure 3:
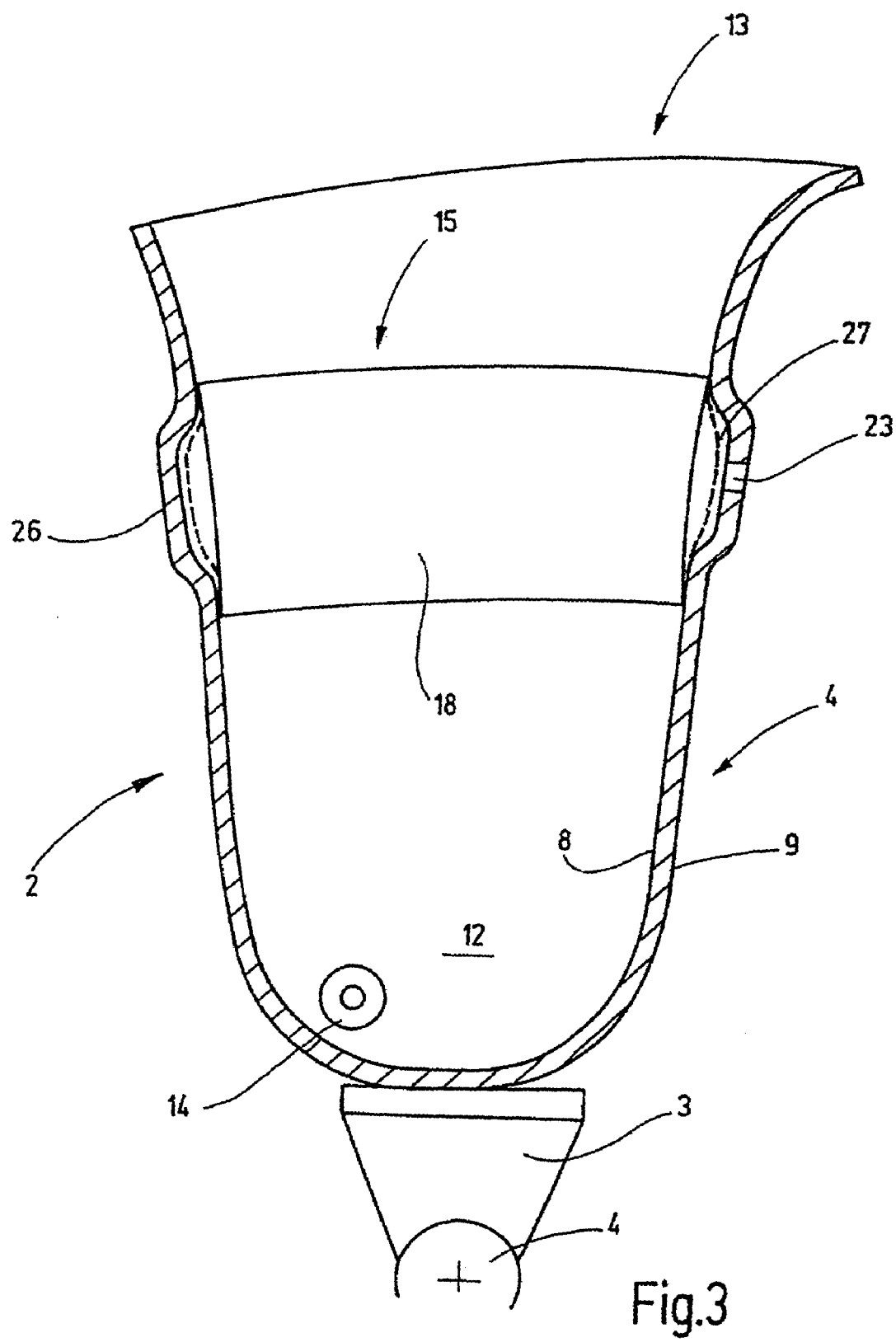
FIG. 3 is a longitudinal section of a prosthetic socket of the invention fitted with an annular groove.

FIG. 3 shows an alternative embodiment that is especially appropriate for prostheses fitted to residual limbs having much soft tissue on all sides.

Figure 2:
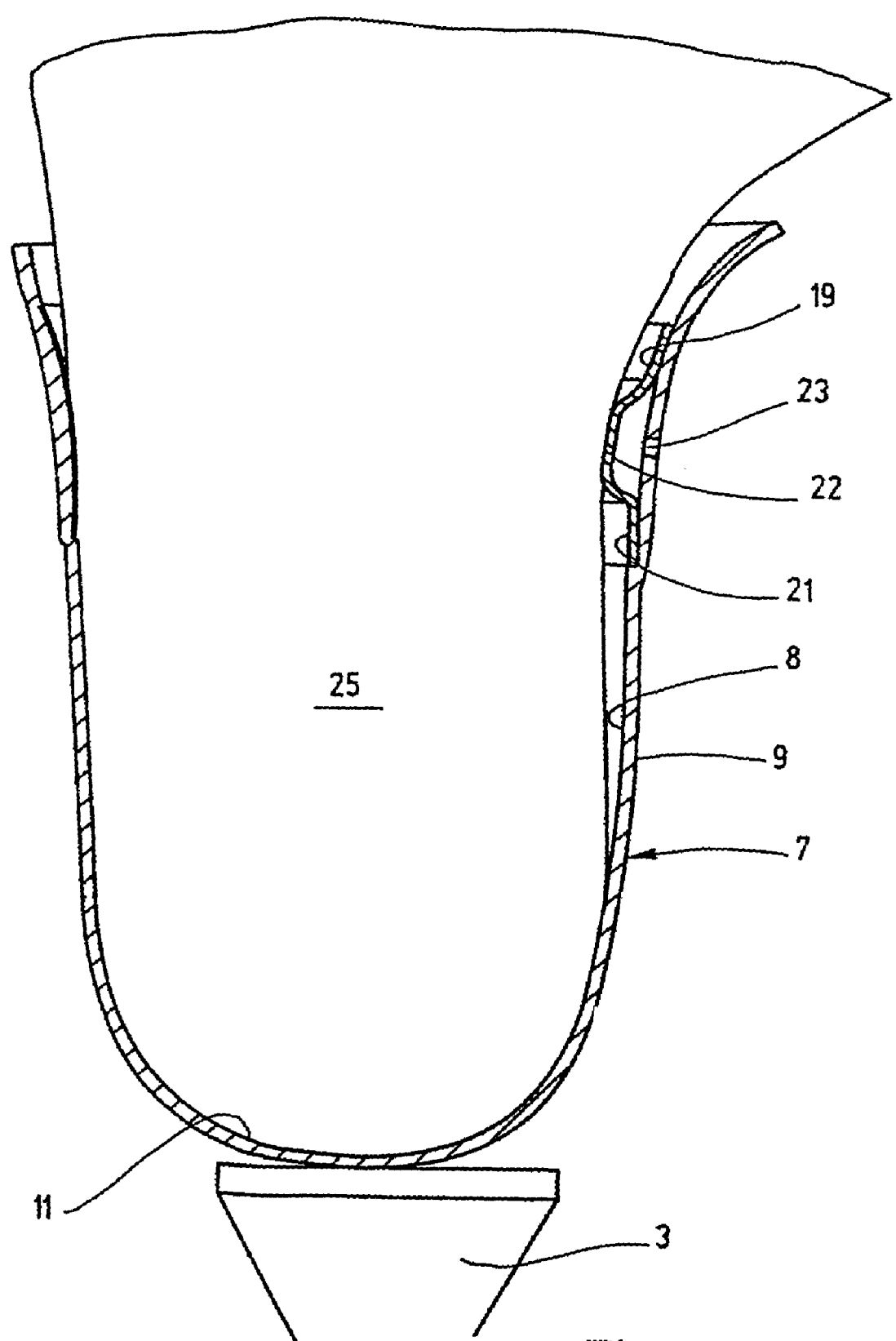
FIG. 2 shows the interaction of the prosthetic socket of the invention with an above-the-knee residual limb.

Unlike the design of FIGS. 1 and 2, the chamber 15 in the embodiment of FIG. 3 is bounded at its outer side by an annular groove or channel defined by an annular or channel-like outwardly pointing protrusion 26 of the socket wall 7. An annular groove 27 is formed in the inner wall 8 and runs circumferentially in it and is covered by the elastic sealing wall 18. The wall 18 spans the annular groove 27 in substantially a stress-free manner and complements the contour of the inside surface 8 in a direction from the distal to the proximal end as if the annular groove 27 were absent.

Again the chamber 15 of this design is vented with external atmospheric air by means of the borehole 23. This embodiment of the above-knee prosthesis operates as follows:

When the residual limb enters the prosthetic socket 2, its tissue, on account of its own elasticity, will force the sealing wall 18 radially outward some distance into the annular space. In this manner the wall 18, just as before, shall reliably rest peripherally against the residual limb, and on the other hand each area of the chamber's inside volume bounded between the annular groove 27 and the wall 18 shall be reliably vented through the borehole 23.

If there occurs a force tending to pull the prosthetic socket 2 from the residual limb, then, as discussed above, a partial vacuum will come into play and will force the zone of the wall 18 against the residual limb and implement an air tight seal.

The embodiment of FIG. 3 provides the advantage of a somewhat simpler manufacturing procedure but on the other hand it is also restricted to treatments which concern residual limbs having much resilient tissue on all sides. If such a condition is not met, this embodiment still is applicable with a gel type elastomer.

The basic concept of a partial-vacuum dependent, self-enhancing seal compression is not restricted to prosthetic sockets such as are shown in FIGS. 1 through 3. This basic principle is also applicable to liners and hence to retrofitting existing prostheses.

Figure 4:
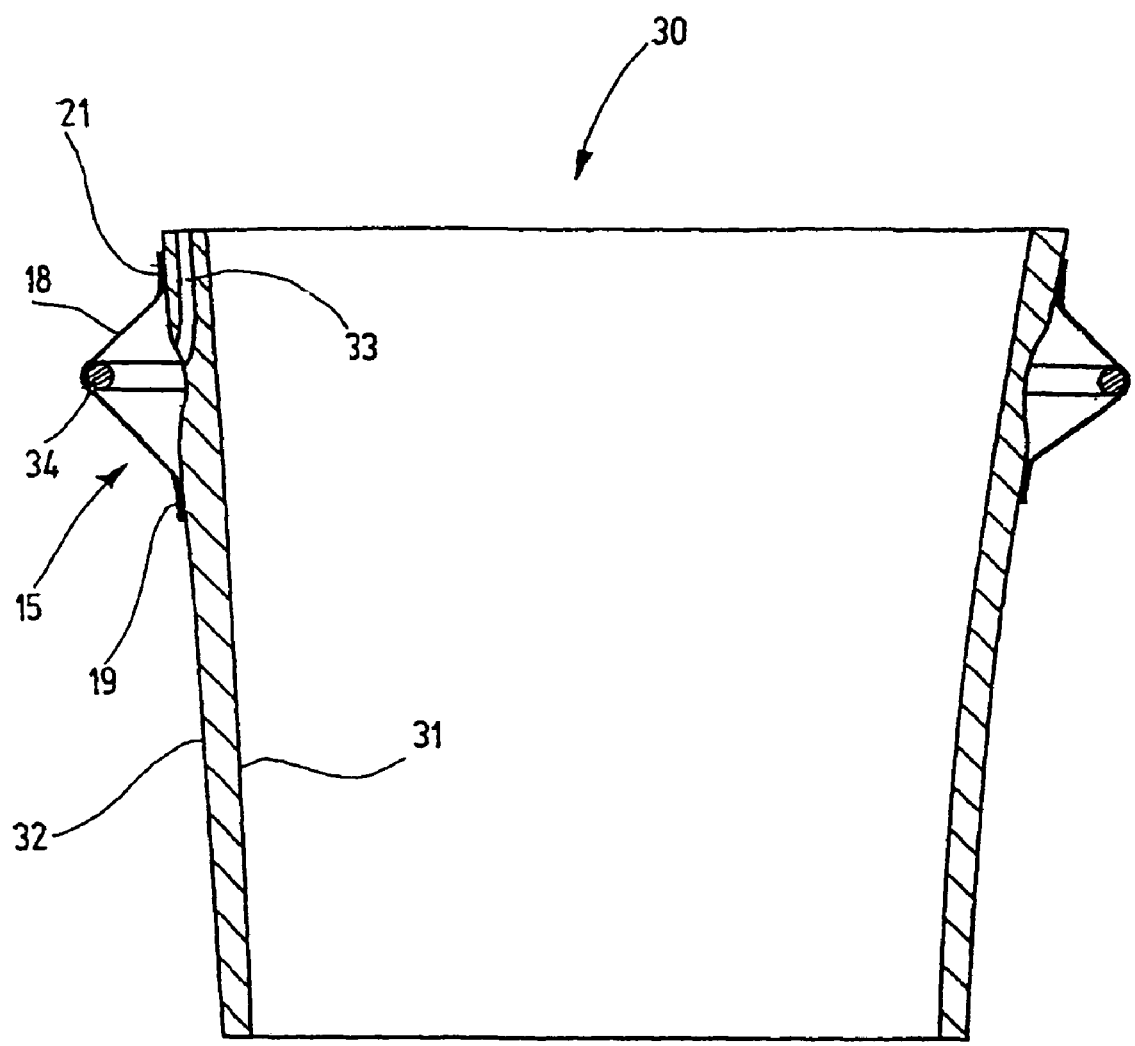
FIG. 4 is a longitudinal section of a sealing sleeve according to the invention applied to an above-the-knee residual limb.

FIG. 4 shows a liner or sleeve 30 according to the present invention configured as a cuff open at its bottom in this example. The sleeve 30 is made of a conventional prosthetic material which on one hand is skin-compatible and on the other hand is radially stretchable.

The sleeve 30 subtends a cuff having an inner side 31 and an outer side 32. The above discussed chamber 15 is located on the outer side 32 of the sleeve near the proximal end of the sleeve and is bounded on one hand by the outer side 32 of the sleeve 30 and on the other hand by an elastically stretchable sealing wall 18. Again, the sealing 18 is adhesively and substantially hermetically bonded along two rim strips 19 and 21 to the outer wall 32.

The pressure balancing conduit venting the inside of chamber 15 is in the form of a duct 33 in the wall of the sleeve 30 and connects the inside of the space 15 to allow air flow to the proximal rim of the sleeve 30. The pressure balancing duct 33 may be designed to comprise additional reinforcing elements in a manner such that it cannot be closed regardless of the load on the sleeve 30. In order to generate the initial sealing force, an elastic ring 34 is configured within the chamber 15 and is radially prestressed outwardly toward the middle zone of the sealing wall 18.

To more clearly show the principles of the present invention, FIG. 4 is not drawn to scale.

The sleeve 30 of the invention is used as follows: The patient pulls the sleeve 30 over the residual limb to the desired height. In this state the inner side 31 of the sleeve 30 rests on the skin in a snug and air tight manner. Next the patient inserts his/her residual limb with the sleeve into the prosthetic socket such as shown in FIG. 1, however without the chamber 15 shown in FIG. 1. As soon as the residual limb has entered deeply enough into the prosthetic socket, the outwardly curving zone of the sealing wall 18 comes to rest against the prosthetic socket's inner side. In this manner a seal is established between the prosthetic socket's inner side and the elastically yielding sealing wall 18.

The sealing effect due to the partial vacuum and the venting of the inside space of the chamber 15 already has been described.

A sock-shaped liner having a distally closed end also may be used in lieu of a cuff-shaped sleeve.

In summary, a prosthetic socket includes an annular chamber located at a distance away from the distal end. The annular chamber is closed on the inside of the prosthetic socket by a contour-conforming sealing wall designed to rest hermetically against the outside of a residual limb. The space between this contour-conforming wall and the hard prosthetic socket is vented with atmospheric air, resulting in self-enhancing compression of the contour conforming sealing wall on the residual limb when a partial vacuum is created between the wall and the distal end in the region of the prosthetic socket.

The invention claimed is:

1. A cup-shaped prosthetic socket for receiving a residual limb,
    said socket comprising a substantially dimensionally stable socket wall forming a thickness and having an outwardly facing outer side and an inwardly facing inner side;
    a substantially dimensionally stable socket distal end connected to the socket wall and jointly with said socket wall bounding a cup-shaped inside volume accessible to receive a residual limb through a proximal insertion opening bounded by a socket rim, the shape of the inside volume adapted to receive a residual limb in close fitting relationship;
    a chamber sealed relative to the inside volume and attached only at a location spaced near the socket proximal insertion opening end and along the inner side of the socket wall, said chamber extending at least some distance in a peripheral direction of the socket and being fitted with a sealing wall facing toward the inside volume of the socket, said sealing wall being made of an air tight, contour-conforming material and adapted to effect a seal between the inside volume relative to a residual limb, said sealing wall extending over a segment of the inwardly facing inner side of the socket between the proximal insertion opening and the distal end of the socket to thereby bound at least a portion of the inside volume of the socket and
    at least one pressure balancing duct formed through the thickness of the socket wall having an inner open end continuously in communication with the chamber and an outer open end that continuously communicates with a source of air that is at least at atmospheric pressure, the inner and outer ends defining orifices formed from the socket wall.

2. Prosthetic socket as claimed in claim 1, wherein said source of air is ambient atmosphere.

3. Prosthetic socket as claimed in claim 1, wherein the chamber comprises an annulus formed as a closed ring in a peripheral direction on the inner side of the socket wall.

4. Prosthetic socket as claimed in claim 1, wherein a wall of the chamber facing the outer side of the prosthetic socket comprises the socket wall.

5. Prosthetic socket as claimed in claim 1, wherein the chamber is between 3 and 6 cm long in a longitudinal direction of the prosthetic socket.

6. Prosthetic socket as claimed in claim 1, wherein the sealing wall is made of a material is elastically stretchable.

7. Prosthetic socket as claimed in claim 1, wherein the sealing wall is configured so as to extend towards the inner volume over a distance substantially corresponding to the length of sealing wall in a peripheral direction of the inside volume of the chamber.

8. Prosthetic socket as claimed in claim 1, wherein said sealing wall comprises a radially prestressed element.

9. Prosthetic socket as claimed in claim 1, wherein said sealing wall bounds an opening which is radially smaller by 1–3 cm than the cross-section of the socket inside volume above and below the chamber location.

10. Prosthetic socket as claimed in claim 1, wherein the pressure balancing duct comprises a bore through the socket wall.

11. Prosthetic socket as claimed in claim 1, comprising a recess defined by the socket wall at the location of the chamber, said recess corresponding to a length of the chamber as seen in the peripheral direction, and wherein the recess is covered by the sealing wall.

12. Prosthetic socket as claimed in claim 11, wherein the recess comprises an annular groove extending along the inner side of the socket wall.

13. Prosthetic socket as claimed in claim 12, wherein the socket wall has a thickness that is substantially the same at all locations including that of the annular groove.

14. A liner which in use is adapted to encircle a residual limb, said liner comprising an outwardly facing outer side and an inwardly facing inner side, said liner having distal and proximal ends,
    a chamber configured on the outer side of the liner a distance away from the distal end and running at least some length in a peripheral direction of the liner, and an outward and outwardly curving sealing wall made of an air tight, contour-conforming material, said sealing wall adapted to seal off the liner against a wall of a prosthetic socket in which the liner may be located while on a residual limb, and
    said liner including at least one pressure balancing duct having open ends and which at one open end enters the chamber and at the other open end continuously communicates with the external atmosphere, and said duct being configured such that it remains air permeable during use;

a tensioning ring located in the chamber and associated with the contour-conforming wall arranged to bias the sealing wall radially outward from the liner over a path substantially corresponding to a length of the sealing wall in a peripheral direction of the liner along of the chamber.

15. Liner as claimed in claim 14, wherein the chamber comprises a closed annular ring and runs in a peripheral direction along the outer side of the liner.

16. Liner as claimed in claim 14, wherein a wall of the chamber facing the outer side of the liner is defined by the liner.

17. Liner as claimed in claim 14, wherein the chamber runs between 3 and 6 cm in a longitudinal direction of the liner.

18. Liner as claimed in claim 14, wherein the material of the sealing wall is elastically stretchable.

19. Liner as claimed in claim 14, wherein the chamber is configured in such manner that in its operational state, the sealing wall defines a cross-section which is 1–3 cm larger in the radial direction than the cross-section of the liner above and or below the chamber.

20. A cup-shaped prosthetic socket for receiving a residual limb,
 said socket comprising a substantially dimensionally stable socket wall having an outwardly facing outer side and an inwardly facing inner side;
 a substantially dimensionally stable socket distal end connected to the socket wall and jointly with said socket wall bounding a cup-shaped inside volume accessible to receive a residual limb through a proximal insertion opening bounded by a socket rim, the shape of the inside volume adapted to receive a residual limb in close fitting relationship;
 a chamber sealed relative to the inside volume and attached at a location spaced from the socket distal end to the inner side of the socket wall, said chamber extending at least some distance in a peripheral direction of the prosthetic socket and being fitted with a sealing wall facing toward the inside volume of the prosthetic socket, said sealing wall being made of an air tight, contour-conforming material and adapted to effect a seal between the inside volume relative to a residual limb;
 at least one pressure balancing duct having one open end that enters the chamber and another open end that continuously communicates with a source of air that is at least at atmospheric pressure, and
 a recess defined by the socket wall at the location of the chamber, said recess corresponding to a length of the chamber as seen in the peripheral direction, and wherein the recess is covered by the sealing wall, wherein the recess comprises an annular groove extending along the inner side of the socket wall;
wherein the socket wall has a thickness that is substantially the same at all locations including that of the annular groove.

* * * * *